US012478107B2

(12) United States Patent
Ou

(10) Patent No.: US 12,478,107 B2
(45) Date of Patent: Nov. 25, 2025

(54) VAPORIZATION TOP BASE, VAPORIZER, AND ELECTRONIC VAPORIZATION DEVICE

(71) Applicant: Jiangmen Moore Technology., Ltd, Guangdong (CN)

(72) Inventor: Guoliang Ou, Jiangmen (CN)

(73) Assignee: Jiangmen Moore Technology., Ltd, Jiangmen (CN)

( * ) Notice: Subject to any disclaimer, the term of this patent is extended or adjusted under 35 U.S.C. 154(b) by 406 days.

(21) Appl. No.: 18/086,980

(22) Filed: Dec. 22, 2022

(65) Prior Publication Data

US 2023/0210189 A1 Jul. 6, 2023

(30) Foreign Application Priority Data

Dec. 30, 2021 (CN) ......................... 202123432678.1

(51) Int. Cl.
*A24F 40/485* (2020.01)
*A24F 40/10* (2020.01)
(Continued)

(52) U.S. Cl.
CPC ............ *A24F 40/485* (2020.01); *A24F 40/10* (2020.01); *A24F 40/42* (2020.01); *A24F 40/46* (2020.01); *A24F 40/48* (2020.01); *A61M 11/042* (2014.02)

(58) Field of Classification Search
CPC ........ A24F 40/485; A24F 40/10; A24F 40/42; A24F 40/46; A24F 40/48
See application file for complete search history.

(56) References Cited

U.S. PATENT DOCUMENTS

2017/0280775 A1 10/2017 Manca et al.
2018/0116291 A1* 5/2018 Monsees ................ A24F 40/42
(Continued)

FOREIGN PATENT DOCUMENTS

CN 211832828 U 11/2020
CN 112471608 A 3/2021
(Continued)

OTHER PUBLICATIONS

Patent Cooperation Treaty, International Search Report and Written Opinion, International Application No. PCT/CN2022/128589 (Dec. 22, 2022).
(Continued)

*Primary Examiner* — Michael H. Wilson
*Assistant Examiner* — Jennifer A Kessie
(74) *Attorney, Agent, or Firm* — Leydig, Voit & Mayer, Ltd.

(57) ABSTRACT

A vaporization top base in communication with a liquid storage cavity of a vaporizer includes: a top base body having a top wall and a side wall surrounding the top wall, the top wall and the side wall encircling to form a vaporization cavity that is independent of the liquid storage cavity and provided with an opening on one end; and at least two liquid feeding channels provided on the top wall, each of the at least two liquid feeding channels being in communication between the liquid storage cavity and the vaporization cavity. A first corner that is arranged close to a central axis of the vaporization cavity and a second corner that is arranged away from the central axis of the vaporization cavity are arranged in each of the liquid feeding channels. The first corner is arranged upstream of the second corner in a liquid inlet direction.

14 Claims, 11 Drawing Sheets

(51) Int. Cl.

| | |
|---|---|
| ***A24F 40/42*** | (2020.01) |
| ***A24F 40/46*** | (2020.01) |
| ***A24F 40/48*** | (2020.01) |
| *A61M 11/04* | (2006.01) |

(56) References Cited

U.S. PATENT DOCUMENTS

| | | | | |
|---|---|---|---|---|
| 2022/0192270 | A1* | 6/2022 | Zeng | A24F 40/10 |
| 2023/0210189 | A1 | 7/2023 | Ou | |

FOREIGN PATENT DOCUMENTS

| | | | |
|---|---|---|---|
| CN | 112545064 | A | 3/2021 |
| CN | 212937921 | U | 4/2021 |
| CN | 113142653 | A | 7/2021 |
| CN | 113647680 | A | 11/2021 |
| CN | 214594164 | U | 11/2021 |
| CN | 214594169 | U | 11/2021 |
| CN | 214802300 | U | 11/2021 |
| CN | 215075499 | U | 12/2021 |
| CN | 113892696 | A | 1/2022 |
| CN | 217161079 | U | 8/2022 |
| WO | 2021142777 | A1 | 7/2021 |
| WO | 2023124498 | A1 | 7/2023 |

OTHER PUBLICATIONS

Patent Cooperation Treaty, International Search Report and Written Opinion, International Application No. PCT/CN2022/117635 (Nov. 30, 2022).

Canadian Patent Office, Office Action in Canadian Patent Application No. 3, 185,439 (May 1, 2024).

* cited by examiner

VAPORIZATION TOP BASE, VAPORIZER, AND ELECTRONIC VAPORIZATION DEVICE

CROSS-REFERENCE TO PRIOR APPLICATION

Priority is claimed to Chinese Patent Application No. 202123432678.1, filed on Dec. 30, 2021, the entire disclosure of which is hereby incorporated by reference herein.

FIELD

This application relates to the field of vaporization technologies, and in particular, to a vaporization top base, a vaporizer including the vaporization top base, and an electronic vaporization device including the vaporizer.

BACKGROUND

An electronic vaporization device generally includes a vaporizer and a power supply component, where the power supply component is configured to supply power to the vaporizer, the vaporizer converts electrical energy into heat energy, and an aerosol-generation substrate is converted by the heat energy into aerosols that can be inhaled by a user. In the related art, in a process that external air enters a liquid storage cavity through a vaporization core, because the viscosity of the aerosol-generation substrate is excessively large, air may form bubbles with different sizes when entering the liquid storage cavity. When there are excessive bubbles or the bubbles are excessively large, the bubbles are likely to gather above a liquid absorbing surface of the vaporization core, and bubbles are stuck in a liquid feeding channel that is in communication with a vaporization top base and the liquid storage cavity. As a result, liquid absorption of the vaporization core is blocked, and dry burning of the vaporization core may be caused due to obstructed liquid feeding, thereby affecting usage by the user and a service life of the vaporizer during use.

SUMMARY

In an embodiment, the present invention provides a vaporization top base in communication with a liquid storage cavity of a vaporizer, the vaporization top base comprising: a top base body comprising a top wall and a side wall surrounding the top wall, the top wall and the side wall encircling to form a vaporization cavity that is independent of the liquid storage cavity and provided with an opening on one end; and at least two liquid feeding channels provided on the top wall, each of the at least two liquid feeding channels being in communication between the liquid storage cavity and the vaporization cavity, wherein a first corner that is arranged close to a central axis of the vaporization cavity and a second corner that is arranged away from the central axis of the vaporization cavity are arranged in each of the liquid feeding channels, and wherein the first corner is arranged upstream of the second corner in a liquid inlet direction.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

Figure 1:
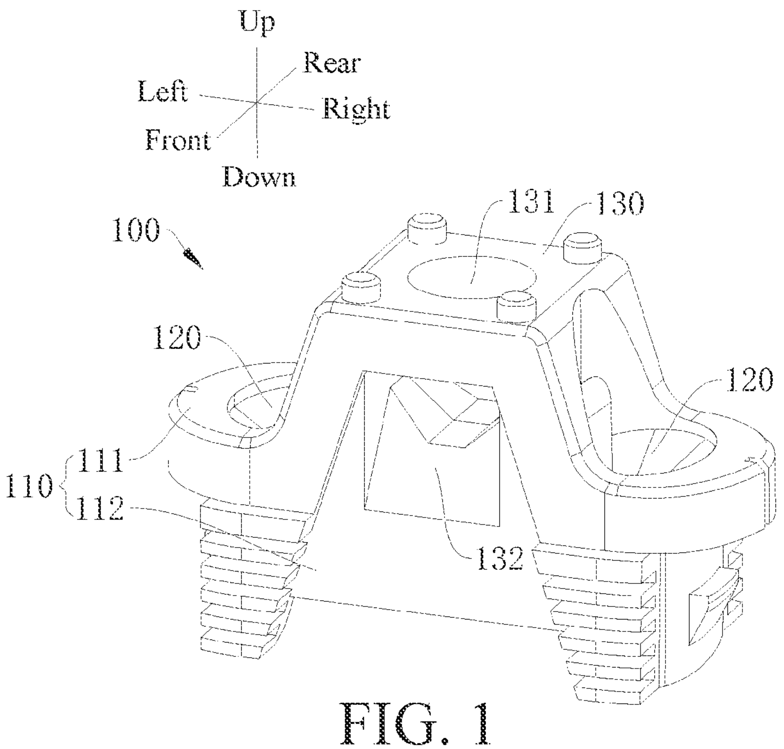
FIG. 1 is a schematic structural diagram of a vaporization top base in an implementation from a perspective according to an embodiment of this application.

In an embodiment, the present invention provides a vaporization top base, a vaporizer, and an electronic vaporization device, to resolve the problem that bubbles are stuck in a liquid feeding channel, so as to improve a service life of the vaporizer and the use experience of a user.

According to an aspect of this application, an embodiment of this application provides a vaporization top base, in communication with a liquid storage cavity of a vaporizer, the vaporization top base including:

- a top base body, including a top wall and a side wall surrounding the top wall, the top wall and the side wall encircling to form a vaporization cavity that is independent of the liquid storage cavity and provided with an opening on one end; and
- at least two liquid feeding channels, provided on the top wall, where each of the liquid feeding channels is in communication between the liquid storage cavity and the vaporization cavity; and
- a first corner that is arranged close to a central axis of the vaporization cavity and a second corner that is arranged away from the central axis of the vaporization cavity are arranged in each of the liquid feeding channels, and the first corner is arranged upstream of the second corner in a liquid inlet direction.

In an embodiment, each of the liquid feeding channels includes a first liquid inlet provided close to the central axis of the vaporization cavity and a second liquid inlet provided away from the central axis of the vaporization cavity; the first liquid inlet is in communication with the second liquid inlet, and a plane in which the first liquid inlet is located is above a plane in which the second liquid inlet is located in the liquid inlet direction; and the first corner is arranged on a side of the first liquid inlet, and the second corner is arranged on a side of the second liquid inlet.

In an embodiment, the vaporization top base further includes a protruding stage arranged protruding from the top wall; and at least a part of the first liquid inlet in each of the liquid feeding channels is provided on the protruding stage, and the second liquid inlet in each of the liquid feeding channels is provided on the top wall.

In an embodiment, an air guide channel is provided on the protruding stage, and all of the liquid feeding channels are provided on a periphery of the air guide channel in a circumferential direction; and the first corner in each of the liquid feeding channels is arranged close to an inner side of the air guide channel, and the second corner in each of the liquid feeding channels is arranged away from an outer side of the air guide channel.

In an embodiment, the air guide channel includes an open end and a closed end opposite to the open end;

the protruding stage is further provided with vent openings provided on two sides of a central axis of the air guide channel in a first direction and configured to communicate the air guide channel with the vaporization cavity; and the first direction is perpendicular to the central axis of the air guide channel.

In an embodiment, a plane in which the closed end of the air guide channel is located and the plane in which the second liquid inlet is located are the same plane or parallel to each other.

In an embodiment, a vaporization core of the vaporizer is accommodated in the vaporization cavity; and in the central axis of the air guide channel, a minimum distance between a surface of a side of the closed end of the air guide channel that faces the vaporization cavity and a top portion of the vaporization core ranges from 1 mm to 3 mm.

In an embodiment, the central axis of the air guide channel and the central axis of the vaporization cavity are parallel to each other and/or overlap with each other.

In an embodiment, in the central axis of the air guide channel, a height of the protruding stage ranges from 1.8 mm to 5.5 mm.

In an embodiment, in the liquid inlet direction, a diameter of a cross-section of a part of each of the liquid feeding channels downstream of the first corner ranges from 2 mm to 4 mm According to another aspect of this application, an embodiment of this application provides a vaporizer, including:

a housing, where a liquid storage cavity and an accommodating cavity that are independent of each other are provided in the housing;

a vaporization base, arranged in the accommodating cavity, where the vaporization base includes a vaporization bottom base and the vaporization top base described above, and the vaporization bottom base is arranged at the opening to cooperate with the vaporization top base to form the vaporization cavity; and a vaporization core, arranged in the vaporization cavity, where each of the liquid feeding channels is configured to guide an aerosol-generation substrate in the liquid storage cavity to the vaporization core.

In an embodiment, an inhalation channel and an air inlet channel are further provided in the housing, the inhalation channel is in communication with a top end of the vaporization cavity, and the air inlet channel is in communication with a bottom end of the vaporization cavity; and a central axis of the air inlet channel and a central axis of the inhalation channel are parallel to each other and/or overlap with each other.

In an embodiment, the vaporizer further includes a seal member, and the seal member is arranged on a top end of the vaporization top base;

a first gap channel is formed between the seal member and the vaporization top base, a second gap channel that is in communication with the air inlet channel is formed between the vaporization base and the accommodating cavity, and the first gap channel is in communication with the air inlet channel through the second gap channel; and a vent hole is further provided on the seal member, and the vent hole is in communication between the liquid storage cavity and the first gap channel, so that the liquid storage cavity is in communication with the air inlet channel.

According to still another aspect of this application, an embodiment of this application provides an electronic vaporization device, including a power supply and the vaporizer described above, where the vaporizer is detachably connected to the power supply.

In the foregoing vaporization top base, the vaporizer, and the electronic vaporization device, the vaporization top base at least includes a top base body and at least two liquid feeding channels. A first corner that is arranged close to the central axis of the vaporization cavity and a second corner that is arranged away from the central axis of the vaporization cavity are arranged in each of the liquid feeding channels, and the first corner is arranged upstream of the second corner in the liquid inlet direction, so that an exit of the liquid feeding channel is enlarged, thereby enlarging an escaping space for bubbles generated when air flows through the liquid feeding channel, resolving the problem that liquid feeding is obstructed, improving the service life of the vaporizer, and improving the use experience of the user.

Other aspects and advantages of the embodiments of this application will be given in the following description, some of which will become apparent from the following description or may be learned from practices of the embodiments of this application.

LIST OF REFERENCE NUMERALS

Vaporization base 10;

Vaporization top base 100;

Top base body 110, Top wall 111, Side wall 112;

Liquid feeding channel 120, First liquid inlet 121, Second liquid inlet 122;

Protruding stage 130, Air guide channel 131, Open end 1311, Closed end 1312, Vent opening 132;

Vaporization bottom base 200;
Housing 20, Inhalation channel 21, Air inlet channel 22;
Vaporization core 30, Seal gasket 31;
Seal member 40, Vent hole 41;
Suction nozzle 50;
Shell 60;
Power supply 70;
Vaporization cavity a, Liquid storage cavity b, Accommodating cavity c;
First central axis M1, Second central axis M2, Third central axis M3, Fourth central axis M4;
First corner t1, Second corner t2;
First plane P1, Second plane P2;
Distance L, Height H, Diameter D;
Liquid inlet direction q, First direction y; and
First gap channel g1, Second gap channel g2.

To make the foregoing objectives, features, and advantages of this application more comprehensible, detailed description is made to specific implementations of the embodiments of this application below with reference to the accompanying drawings. In the following descriptions, a lot of specific details are provided to help comprehensively understand the embodiments of this application. It should be understood that the specific embodiments described herein are only used for explaining this application, and are not used for limiting this application. The embodiments of this application can be implemented in many manners different from that described herein, and a person skilled in the art may make similar improvements without departing from the essence of the content of the present disclosure. Therefore, the embodiments of this application are not limited by the specific embodiments disclosed below.

It may be understood that, the terms "first" and "second" used in this application are used for describing various professional terms, and shall not be understood as indicating or implying relative significance or implicitly indicating the number of indicated technical features. Unless otherwise specified, the professional terms are not limited by the terms. The terms are merely used for distinguishing one professional term from another professional term. For example, in a case without departing from the scope of this application, a first liquid inlet and a second liquid inlet are different liquid inlets, a first central axis, a second central axis, a third central axis, and a fourth central axis are different central axes, a first corner and a second corner are different corners, a first plane and a second plane are different planes, and a first gap channel and a second gap channel are different gap channels. In the description of this application, "a plurality of" and "several" mean at least two, such as two and three, unless otherwise explicitly and specifically defined.

In the description of the embodiments of this application, unless otherwise explicitly specified and defined, terms such as "mounted", "connected", "connection", and "fixed" should be understood in a broad sense. For example, the connection may be a fixed connection, a detachable connection, or an integral connection; or the connection may be a mechanical connection or an electrical connection; or the connection may be a direct connection, an indirect connection through an intermediate medium, or internal communication between two elements or mutual action relationship between two elements, unless otherwise explicitly specified. A person of ordinary skill in the art may understand the specific meanings of the foregoing terms in the embodiments of this application according to specific situations.

In the description of the embodiments of this application, unless otherwise explicitly specified or defined, that the first feature is "above" or "below" the second feature may be that the first feature is in a direct contact with the second feature, or the first feature is in an indirect contact with the second feature through an intermediate medium. In addition, that the first feature is "above", "over", or "on" the second feature may be that the first feature is directly above or obliquely above the second feature, or may merely indicate that the horizontal position of the first feature is higher than that of the second feature. That the first feature is "below", "under", or "beneath" the second feature may be that the first feature is directly below or obliquely below the second feature, or may merely indicate that the horizontal position of the first feature is lower than that of the second feature.

It should be noted that, when an element is referred to as "being fixed to" or "being arranged on" another element, the element may be directly on the another element, or an intermediate element may be present. When an element is considered to be "connected to" another element, the element may be directly connected to the another element, or an intermediate element may also be present.

Unless otherwise defined, meanings of all technical and scientific terms used in this application are the same as that usually understood by a person skilled in the technical field to which this application belongs. In this application, terms used in the specification of this application are merely intended to describe objectives of the specific embodiments, but are not intended to limit this application.

An electronic vaporization device generally includes a vaporizer and a power supply component, where the power supply component is configured to supply power to the vaporizer, the vaporizer converts electrical energy into heat energy, and an aerosol-generation substrate is converted by the heat energy into aerosols that can be inhaled by a user. In this process, after liquid absorption, a vaporization core heats and vaporizes the aerosol-generation substrate through a heating element. There is a gap in the vaporization core, liquid absorption is performed continuously while the vaporization core performs vaporization, and external air enters a liquid storage cavity through the gap (or another gap, for example, another vent structure formed by some structures and a liquid storage shell) of the vaporization core.

The inventor of this application notices that, in a process that the external air enters the liquid storage cavity through the vaporization core, because the viscosity of the aerosol-generation substrate is excessively large, air may form bubbles with different sizes when entering the liquid storage cavity. When there are excessive bubbles or the bubbles are excessively large, the bubbles are likely to gather above a liquid absorbing surface of the vaporization core, and bubbles are stuck in a liquid feeding channel that is in communication with a vaporization top base and the liquid storage cavity. As a result, liquid absorption of the vaporization core is blocked, and dry burning of the vaporization core may be caused due to obstructed liquid feeding, thereby affecting usage by the user and a service life of the vaporizer during use.

Based on this, in the embodiments of this application, the structure of the liquid feeding channel of the vaporization top base is changed, to resolve the problem that bubbles are stuck in the liquid feeding channel. Related description is made on the vaporization top base provided in the embodiments of this application below with reference to related description of some embodiments.

It should be noted that, the vaporization top base disclosed in the embodiments of this application may be applied to a medical vaporization device, or may be applied to an air humidifier, or may be applied to some devices that a vaporizer needs to be used such as an e-cigarette, which is not specifically limited in the embodiments of this application. A description is made below by using the structure of the vaporization top base in some embodiments as an example, but this application is not limited thereto.

Figure 2:
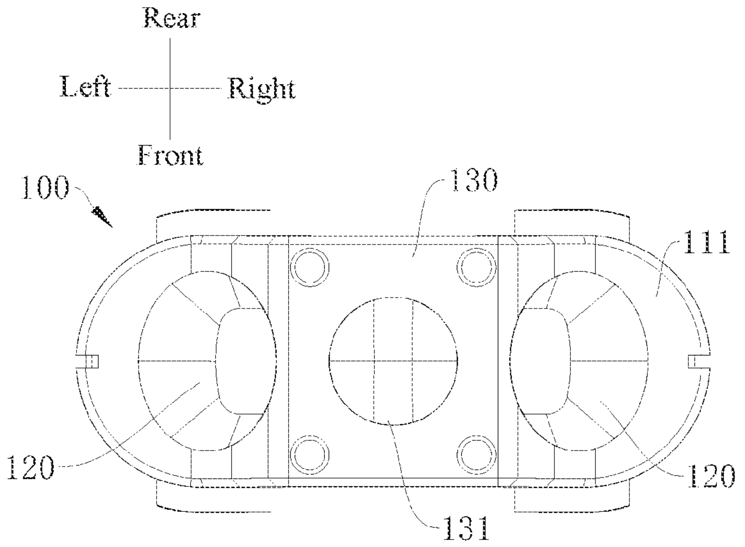
FIG. 2 is a schematic structural diagram of a vaporization top base in an implementation from another perspective according to an embodiment of this application.
Figure 3:
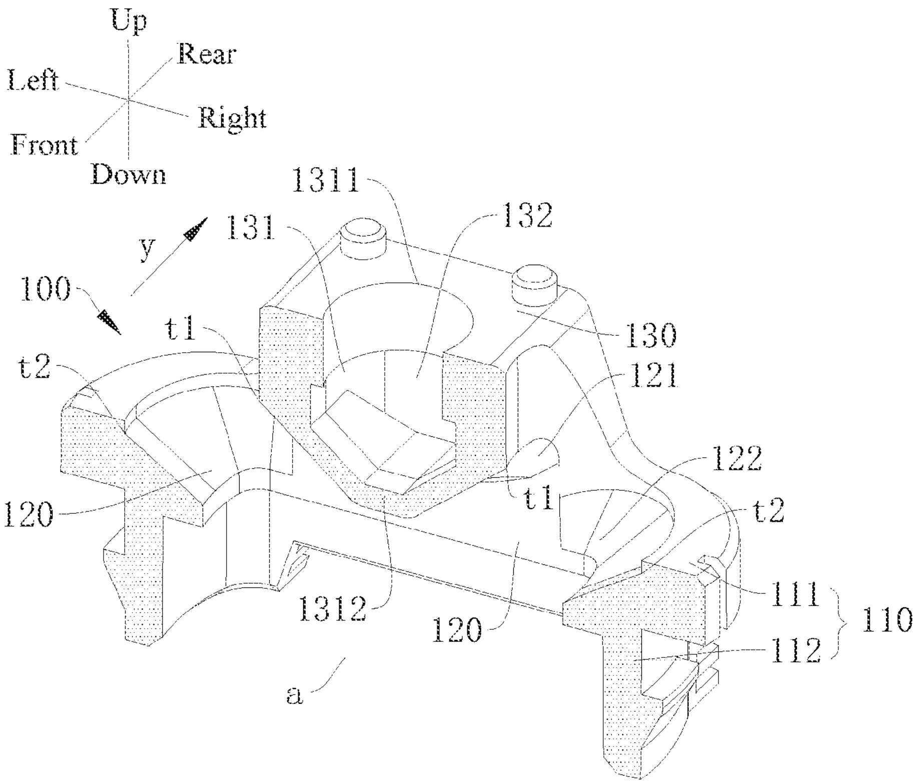
FIG. 3 is a schematic cross-sectional structural view of a vaporization top base in an implementation from a perspective according to an embodiment of this application.
Figure 4:
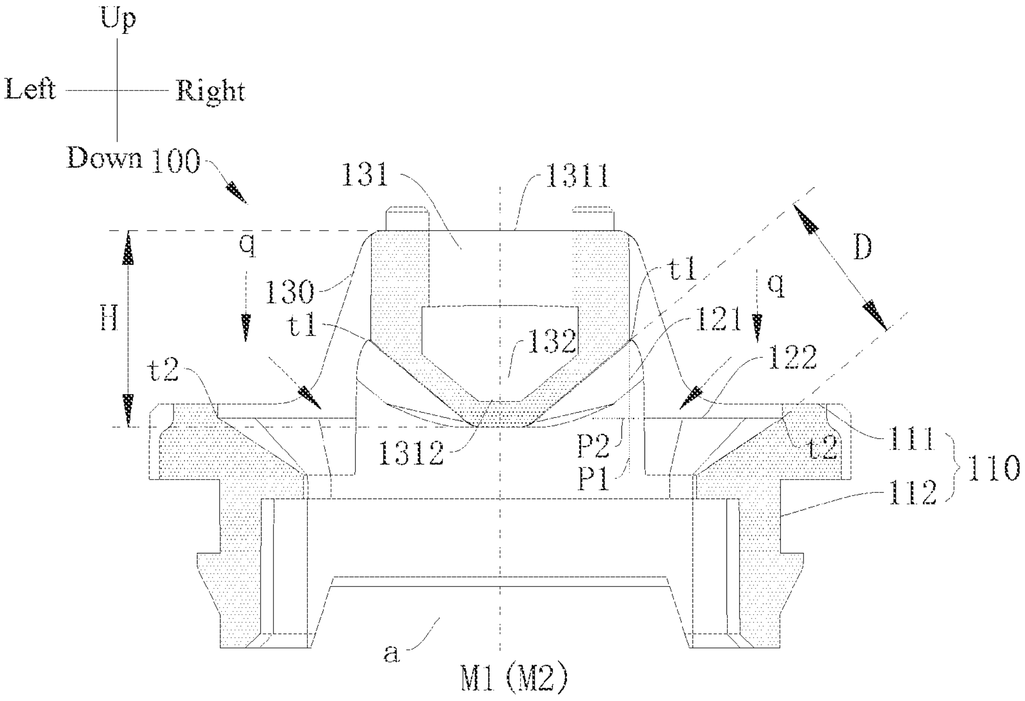
FIG. 4 is a schematic cross-sectional structural view of a vaporization top base in an implementation from another perspective according to an embodiment of this application.

FIG. 1 is a schematic structural diagram of a vaporization top base 100 in an implementation from a perspective according to an embodiment of this application. FIG. 2 is a schematic structural diagram of a vaporization top base 100 in an implementation from another perspective according to an embodiment of this application. FIG. 3 is a schematic cross-sectional structural view of a vaporization top base 100 in an implementation from a perspective according to an embodiment of this application. FIG. 4 is a schematic cross-sectional structural view of a vaporization top base 100 in an implementation from another perspective according to an embodiment of this application. For ease of description, the accompanying drawings only show parts relevant to the embodiments of this application.

For ease of understanding, as shown in FIG. 1, the top of the drawing is defined as the top, the bottom of the drawing is defined as the bottom, the left to the inward of the drawing is defined as the left, the right to the outward of the drawing is defined as the right, the left to the outward of the drawing is defined as the front side, and the right to the inward of the drawing is defined as the rear side. The following drawings follow the directions defined relative to the structure provided in the embodiment of FIG. 1. It should be noted that, the foregoing definitions are merely used for description, and should not be understood as a limitation to this application. It may be understood that, FIG. 2 is a top view of FIG. 1, FIG. 3 is a three-dimensional cross-sectional view of FIG. 1, and FIG. 4 is a schematic front cross-sectional view of FIG. 1.

Referring to FIG. 1 and FIG. 2, an embodiment of this application provides a vaporization top base 100. The vaporization top base 100 is in communication with a liquid storage cavity b of a vaporizer, the liquid storage cavity b is configured to store an aerosol-generation substrate, and the aerosol-generation substrate may be liquid such as e-liquid. The vaporization top base 100 includes a top base body 110 and at least two liquid feeding channels 120. The top base body 110 includes a top wall 111 and a side wall 112 surrounding the top wall 111, the top wall 111 and the side wall 112 encircle to form a vaporization cavity a that is independent of the liquid storage cavity b and provided with an opening on one end. All the liquid feeding channels 120 are provided on the top wall 111, and each liquid feeding channel 120 is in communication between the liquid storage cavity b and the vaporization cavity a. For example, FIG. 1 to FIG. 4 exemplarily show a situation that two liquid feeding channels 120 are provided, where one liquid feeding channel 120 is provided on a left side, and the other liquid feeding channel 120 is provided on a right side of the vaporization top base 100. Certainly, a plurality of liquid feeding channels 120 may also be provided on each side, which is set according to an actual use situation and is not specifically limited in the embodiments of this application.

Referring to FIG. 3 and FIG. 4 in combination with FIG. 1 and FIG. 2, a central axis of the vaporization cavity a is defined as first central axis M1, a first corner t1 that is arranged close to the first central axis M1 and a second corner t2 that is arranged away from the central axis of the vaporization cavity a are arranged in each liquid feeding channel 120, and the first corner t1 is arranged upstream of the second corner t2 in a liquid inlet direction q (namely, a direction entering the vaporization cavity a from top to bottom shown in the figure). If the first corner t1 and the second corner t2 are arranged on the same horizontal line, an exit of the liquid feeding channel 120 may be decreased. As a result, the aerosol-generation substrate may be blocked during turning, leading to obstructed liquid feeding. FIG. 4 is used as an example, in the liquid inlet direction q, because the first corner t1 is arranged upstream of the second corner t2, that is, there is a height H difference between the first corner t1 and the second corner t2 in an up-down direction, the aerosol-generation substrate may be dispersed at the first corner t1 and the second corner t2, thereby enlarging a liquid inlet channel and avoiding blocking caused by simultaneously turning. In this way, by increasing the flow of the aerosol-generation substrate and enlarging an escaping space for bubbles generated when air flows through the exit of the liquid feeding channel 120, the obstructed liquid feeding is resolved, a service life of the vaporizer is improved, and the use experience of the user is improved.

It should be noted that, the exit of the liquid feeding channel 120 may incline toward the first central axis M1 or may incline to a direction away from the first central axis M1. That is, the first corner t1 and the second corner t2 may turn an inner wall of the liquid feeding channel 120 to the first central axis M1, and the first corner t1 and the second corner t2 may also turn the inner wall of the liquid feeding channel 120 to a direction away from the first central axis M1. Certainly, the first corner t1 and the second corner t2 may also turn to different directions. For example, as shown in FIG. 4, FIG. 4 exemplarily shows a situation that the first corner t1 and the second corner t2 turn to the same direction and both turn to the first central axis. The foregoing manners may be selected according to an actual use situation, which is not specifically limited in the embodiments of this application.

In some embodiments, still referring to FIG. 3 and FIG. 4, each liquid feeding channel 120 includes a first liquid inlet 121 provided close to the central axis of the vaporization cavity a and a second liquid inlet 122 provided away from the central axis of the vaporization cavity a, and the first liquid inlet 121 is in communication with the second liquid inlet 122. A plane in which the first liquid inlet 121 is located is defined as a first plane P1, and a plane in which the second liquid inlet 122 is located is defined as a second plane P2. In the liquid inlet direction q, the first plane P1 is above the second plane P2. That is, in the up-down direction before liquid inlet, the first plane P1 is above the second plane P2, and in the up-down direction after liquid inlet, the first plane P1 is below the second plane P2. The first corner t1 is arranged on a side of the first liquid inlet 121, and the second corner t2 is arranged on a side of the second liquid inlet 122. Because the first liquid inlet 121 and the second liquid inlet 122 are located in different planes, the liquid inlets are enlarged when compared with a situation that the liquid inlets are liquid inlets in the same plane, so that a liquid feeding process of the aerosol-generation substrate before reaching the corner is smoother.

In some embodiments, still referring to FIG. 3 and FIG. 4 in combination with FIG. 1 and FIG. 2, the vaporization top base 100 further includes a protruding stage 130 arranged protruding from the top wall 111 (the situation that the protruding stage 130 extends upward exemplarily shown in the figure). At least a part of the first liquid inlet 121 in each liquid feeding channel 120 is provided on the protruding stage 130, and the second liquid inlet 122 in each liquid feeding channel is provided on the top wall 111. In this way, due to the arrangement of the protruding stage 130, not only the liquid inlets may be enlarged, but also weight reduction may be implemented. Certainly, in some other embodiments, the protruding stage 130 may not be arranged, and only the first liquid inlet 121 and the second liquid inlet 122 located in different planes are provided on the top wall 111 to enlarge the amount of liquid inlet. The foregoing manners may be selected according to an actual use situation, which is not specifically limited in the embodiments of this application.

In some embodiments, still referring to FIG. 3 and FIG. 4 in combination with FIG. 1 and FIG. 2, an air guide channel 131 is provided on the protruding stage 130, and all of the liquid feeding channels 120 are provided on a periphery of the air guide channel 131 in a circumferential direction. The first corner t1 in each liquid feeding channel 120 is arranged close to an inner side of the air guide channel 131, and the second corner t2 in each liquid feeding channel is arranged away from an outer side of the air guide channel 131. For example, FIG. 1 to FIG. 4 exemplarily show a situation that two liquid feeding channels 120 are provided, and the two liquid feeding channels 120 are respectively arranged on a left side and a right side of the air guide channel 131. Certainly, an additional number of liquid feeding channels 120 may be also arranged surrounding the air guide channel 131, which may be selected according to an actual situation and is not specifically limited in the embodiments of this application. In this way, space may be utilized effectively.

In some embodiments, still referring to FIG. 3 and FIG. 4, the air guide channel 131 includes an open end 1311 (namely, an upper end of the air guide channel 131 exemplarily shown in FIG. 3 and FIG. 4, and the upper end includes an opening) and a closed end 1312 opposite to the open end 1311 (namely, a lower end of the air guide channel 131 exemplarily shown in FIG. 3 and FIG. 4). A central axis of the air guide channel 131 is defined as a second central axis M2, the protruding stage 130 is further provided with vent openings 132 provided on two sides of the second central axis M2 in a first direction y (a front-rear direction exemplarily shown in FIG. 3 and FIG. 4), and the vent openings 132 are configured to communicate the air guide channel 131 with a vent opening 132 of the vaporization cavity a. The first direction y is perpendicular to the central axis of the air guide channel 131. In this way, aerosols in the vaporization cavity a enter the air guide channel 131 through the vent openings 132, so that space is effectively utilized and the design is provided for ease of use of the user. Specifically, in some embodiments, still referring to FIG. 4, a plane in which the closed end 1312 of the air guide channel 131 is located and the plane in which the second liquid inlet 122 is located are the same plane or parallel to each other. In this way, a length of the air guide channel 131 may be set according to an actual use situation.

In some embodiments, still referring to FIG. 4 in combination with FIG. 9 mentioned below, a vaporization core 30 of the vaporizer is accommodated in the vaporization cavity a. In the second central axis M2 (namely, the up-down direction exemplarily shown in FIG. 4), a minimum distance L between a surface of a side of the closed end 1312 of the air guide channel 131 that faces the vaporization cavity a and a top portion of the vaporization core 30 ranges from 1 mm to 3 mm. In this way, by designing the distance L between the closed end 1312 of the air guide channel 131 and the top portion of the vaporization core 30, the escaping space for the bubbles and a space of the vaporization cavity a provided on the top portion of the vaporization core 30 are further enlarged, thereby resolving the problem of obstructed liquid feeding.

In some embodiments, still referring to FIG. 4, the central axis of the air guide channel 131 and the central axis of the vaporization cavity a are parallel to each other and/or overlap with each other. That is, the first central axis M1 and the second central axis M2 are parallel to each other and/or overlap with each other. FIG. 4 exemplarily shows a situation that the first central axis M1 and the second central axis M2 overlap with each other. In this way, the structure helps aerosols in the vaporization cavity a enter the air guide channel 131 and is provided for ease of use of the user.

In some embodiments, still referring to FIG. 4, in the central axis of the air guide channel 131, namely, in the second central axis M2, a height H of the protruding stage 130 ranges from 1.8 mm to 5.5 mm. In this way, not only the liquid inlet of the liquid feeding channel 120 may be enlarged for ease of liquid feeding, but also the space of the air guide channel 131 may be increased for ease of air guiding.

In some embodiments, still referring to FIG. 4, in the liquid inlet direction q, a diameter D of a cross-section of a part of each liquid feeding channel 120 downstream of the first corner t1 ranges from 2 mm to 4 mm. In this way, a size by which the escaping space for the bubbles needs to be enlarged may be obtained by designing a size of the diameter D of the corresponding cross-section.

Figure 5:
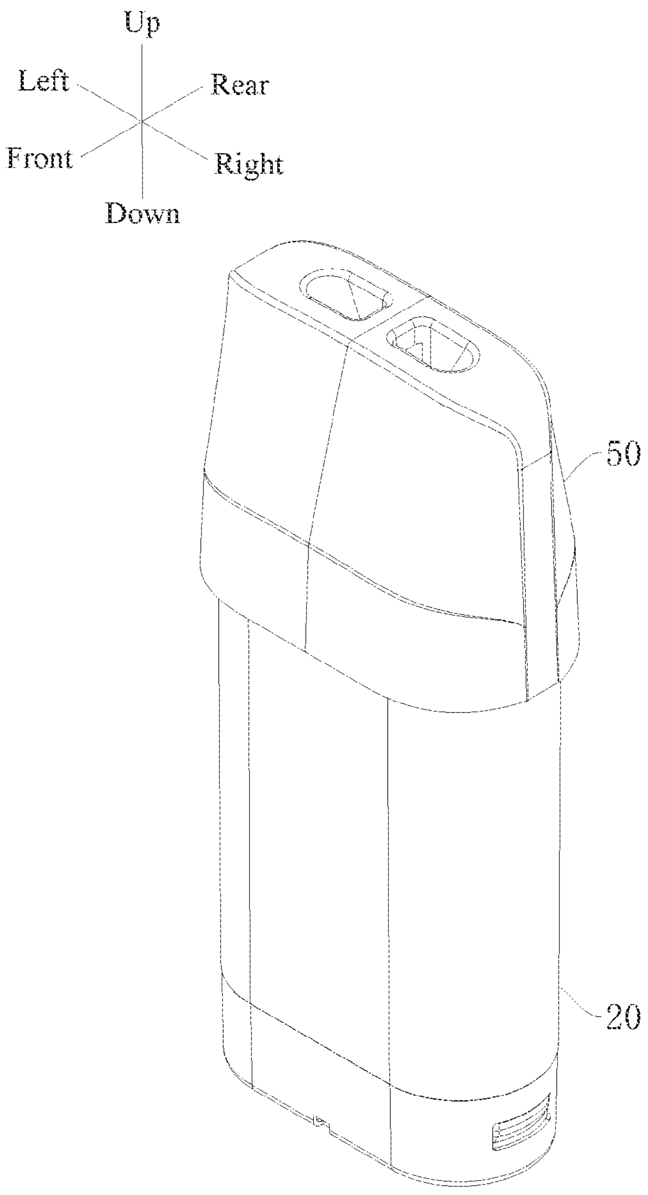
FIG. 5 is a schematic structural diagram of vaporizer in an implementation according to an embodiment of this application.
Figure 6:
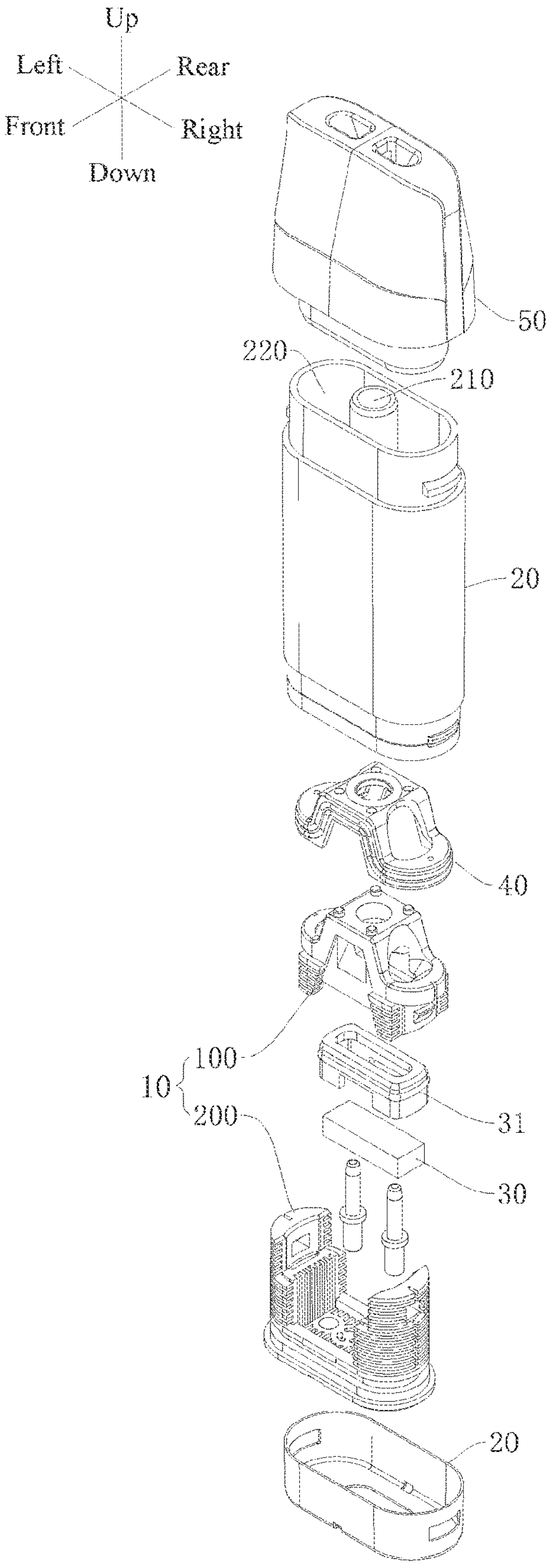
FIG. 6 is a schematic exploded structural view of a vaporizer in an implementation according to an embodiment of this application.
Figure 7:
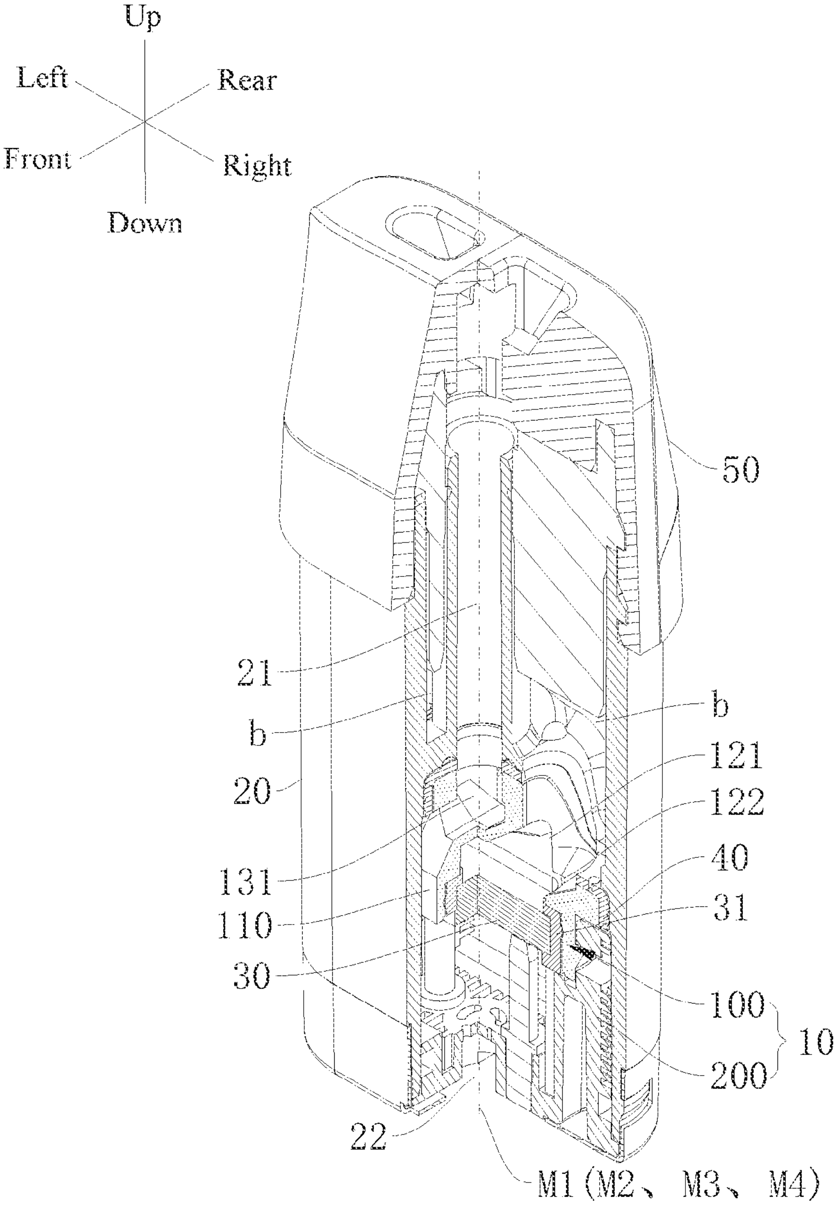
FIG. 7 is a schematic cross-sectional structural view of a vaporizer in an implementation from a perspective according to an embodiment of this application.
Figure 8:
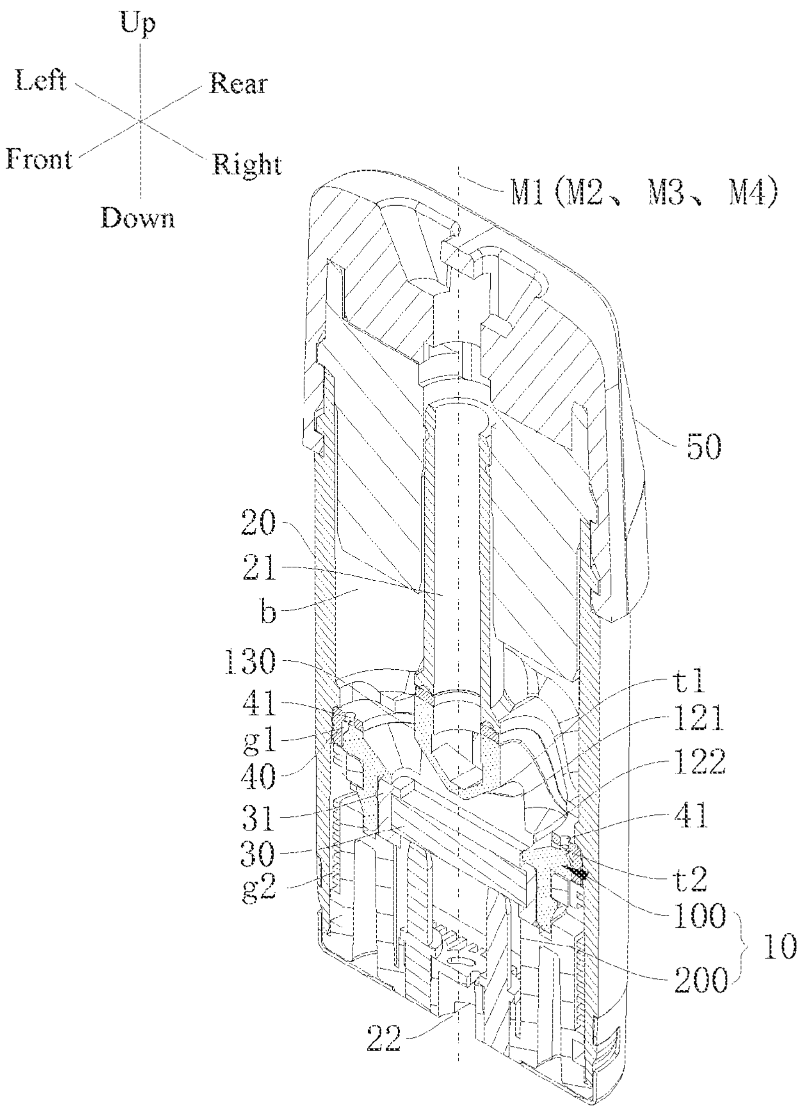
FIG. 8 is a schematic cross-sectional structural view of a vaporizer in an implementation from another perspective according to an embodiment of this application.

FIG. 5 is a schematic structural diagram of vaporizer in an implementation according to an embodiment of this application. FIG. 6 is a schematic exploded structural view of a vaporizer in an implementation according to an embodiment of this application. FIG. 7 is a schematic cross-sectional structural view of a vaporizer in an implementation from a perspective according to an embodiment of this application. FIG. 8 is a schematic cross-sectional structural view of a vaporizer in an implementation from another perspective according to an embodiment of this application. For ease of description, the accompanying drawings only show parts relevant to the embodiments of this application.

Based on the same inventive concept, as shown in FIG. 5 to FIG. 8, an embodiment of this application provides a vaporizer, and the vaporizer includes a housing 20, a vaporization base 10, and a vaporization core 30. In combination with FIG. 9 and FIG. 10 shown in the following description, a liquid storage cavity b and an accommodating cavity c that are independent of each other are provided in the housing 20, to implement different operation processes for ease of liquid feeding. The vaporization base 10 is arranged in the accommodating cavity c. The vaporization base 10 includes a vaporization bottom base 200 and the vaporization top base 100 in the foregoing embodiments, and the vaporization bottom base 200 is arranged at the opening to cooperate with the vaporization top base 100 to form the vaporization cavity a. The vaporization core 30 is arranged in the vaporization cavity a, and a seal gasket 31 may be arranged outside the vaporization core 30 for ease of mounting and liquid absorption of the vaporization core 30. The liquid feeding channel 120 is configured to guide an aerosol-generation substrate in the liquid storage cavity b to the vaporization core 30. In this way, because the vaporization top base 100 described in the foregoing embodiments is used, liquid feeding in the vaporizer is smooth, and the liquid absorption process of the vaporization core 30 is improved to prevent the vaporization core 30 from dry burning, thereby improving the service life of the vaporizer and the use experience of the user.

In some embodiments, still referring to FIG. 7 and FIG. 8, an inhalation channel 21 and an air inlet channel 22 are further provided in the housing 20, the inhalation channel 21 is in communication with a top end of the vaporization cavity a, and the air inlet channel 22 is in communication with a bottom end of the vaporization cavity a. That is, the air inlet channel 22 is provided on a bottom side of the vaporization cavity a, and the inhalation channel 21 is provided on a top side of the vaporization cavity a. Optionally, one end of the inhalation channel 21 is in communication with the open end 1311 of the air guide channel 131 described in the foregoing embodiments, and the other end of the inhalation channel 21 is in communication with a suction nozzle 50, to implement an inhalation process. A central axis of the air inlet channel 22 is defined as a third central axis M3, a central axis of the inhalation channel 21 is defined as a fourth central axis M4, and the third central axis M3 and the fourth central axis M4 are parallel to each other and/or overlap with each other. Specifically, the third central axis M3 and the fourth central axis M4 may be both arranged vertically or may be arranged obliquely at an angle. For example, FIG. 7 and FIG. 8 exemplarily show a situation that the first central axis M1, the second central axis M2, the third central axis M3, and the fourth central axis M4 are all arranged vertically and overlap with each other. The central axes may be set according to an actual use situation, which are not specifically limited in the embodiments of this application.

Figure 9:
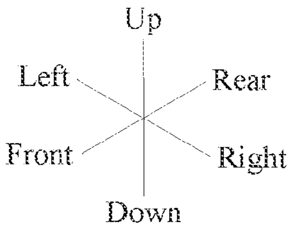
FIG. 9 is a schematic partial enlarged structural view of FIG. 8.
Figure 9:
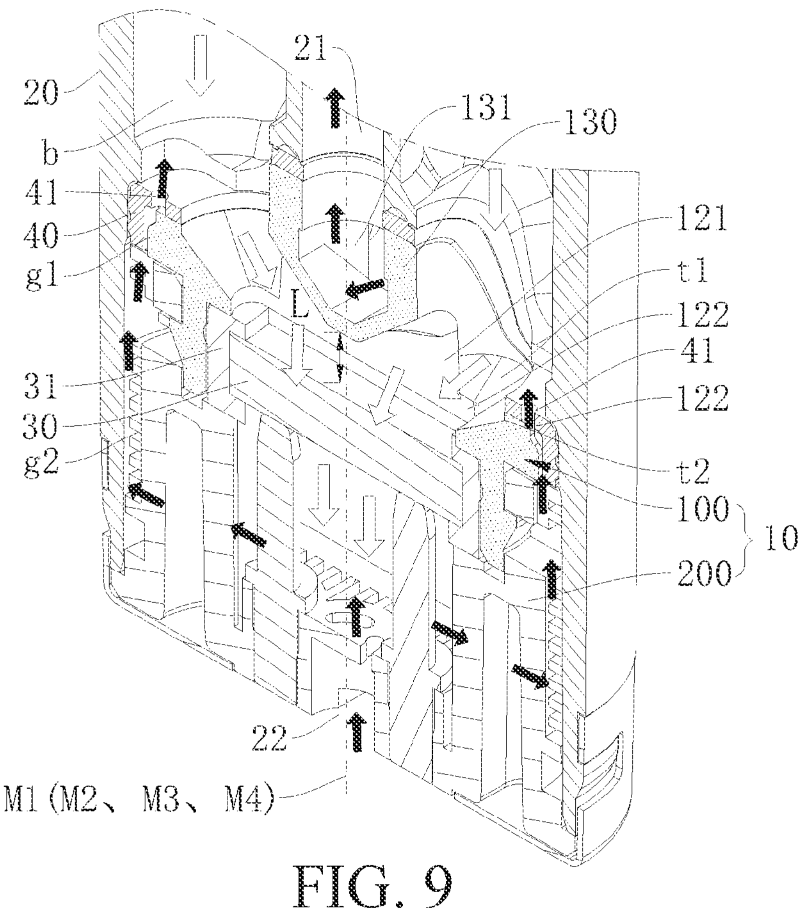
Figure 10:
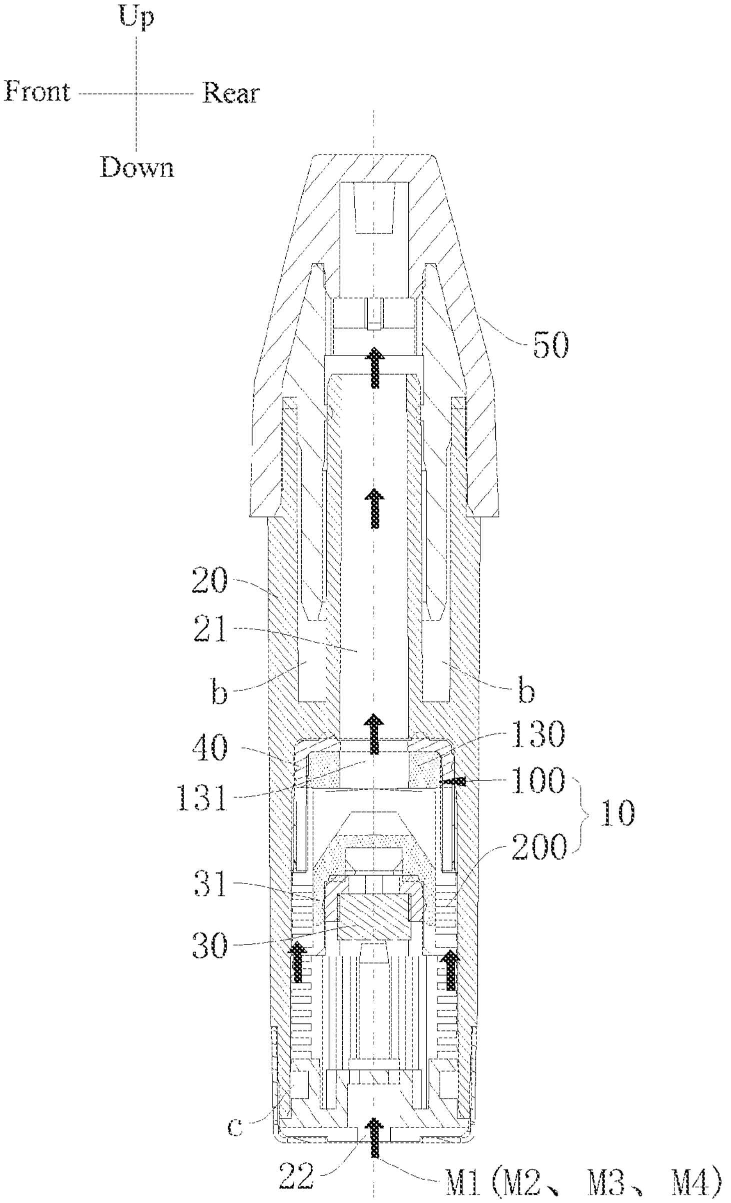
FIG. 10 is a schematic cross-sectional structural view of a vaporizer in an implementation from still another perspective according to an embodiment of this application.

FIG. 9 is a schematic partial enlarged structural view of FIG. 8. FIG. 10 is a schematic cross-sectional structural view of a vaporizer in an implementation from still another perspective according to an embodiment of this application. For ease of description, the accompanying drawings only show parts relevant to the embodiments of this application.

Referring to FIG. 9 and FIG. 10 in combination with FIG. 8, the vaporizer further includes a seal member 40, and the seal member 40 is arranged on a top end of the vaporization top base 100. A first gap channel g1 is formed between the seal member 40 and the vaporization top base 100, a second gap channel g2 in communication with the air inlet channel 22 is formed between the vaporization base 10 and the accommodating cavity c, and the first gap channel g1 is in communication with the air inlet channel 22 through the second gap channel g2. A vent hole 41 is further provided on the seal member 40, and the vent hole 41 is in communication between the liquid storage cavity b and the first gap channel g1, so that the liquid storage cavity b is in communication with the air inlet channel 22. FIG. 9 and FIG. 10 are used as an example, where black box arrows indicate a liquid feeding process, and black arrows indicate an inhalation and air inlet process. The aerosol-generation substrate flows into the liquid feeding channel 120 from the liquid storage cavity b, and the liquid feeding channel 120 guides the aerosol-generation substrate to a vaporization surface of the vaporization core 30 arranged in the vaporization cavity a. When a heating body in the vaporizer is powered on to convert electrical energy into heat energy, liquid absorbed by the vaporization core 30 is vaporized to form aerosols and the aerosols are discharged into the vaporization cavity a. when an inhalation action generating an airflow is performed at the suction nozzle 50, the aerosols in the vaporization cavity a enters the inhalation channel 21 and reaches the suction nozzle 50 to be inhaled by the user. Meanwhile, a part of air entering the air inlet channel 22 may flow through the second gap channel g2, the first gap channel g1, and the vent hole 41 sequentially to enter the liquid storage cavity b. In this way, ventilation of the liquid storage cavity b may be improved through the vent hole 41, thereby further resolving the problem of stuck bubbles.

Figure 11:
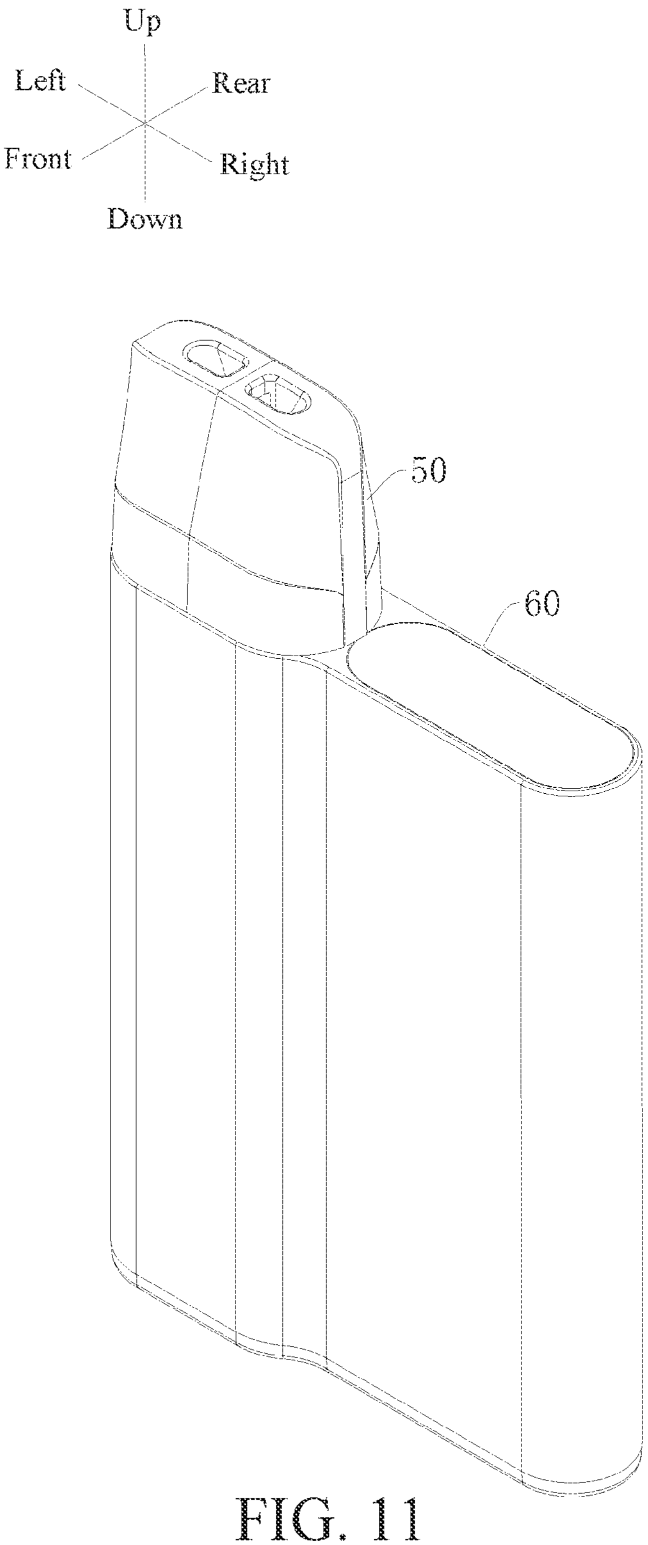
FIG. 11 is a schematic structural diagram of an electronic vaporization device in an implementation according to an embodiment of this application.
Figure 12:
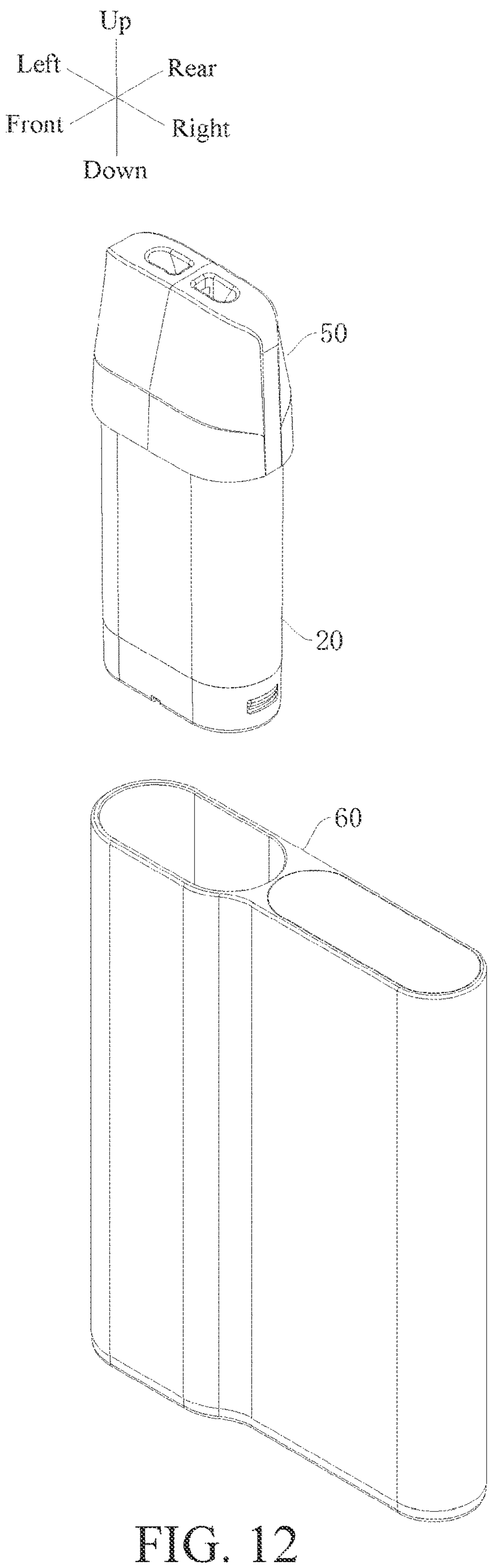
FIG. 12 is a schematic partial exploded structural view of an electronic vaporization device in an implementation according to an embodiment of this application.
Figure 13:
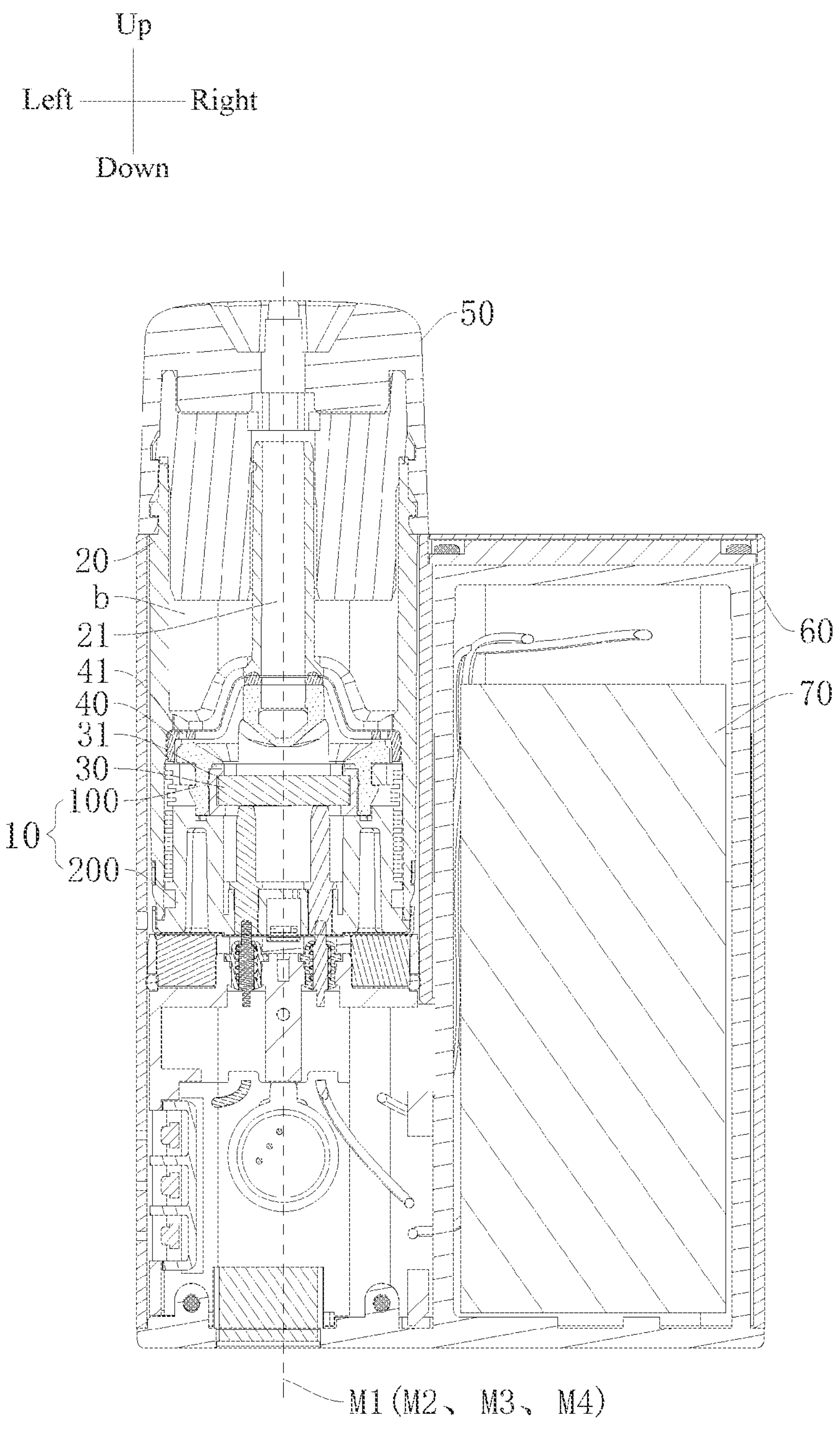
FIG. 13 is a schematic cross-sectional structural view of an electronic vaporization device in an implementation according to an embodiment of this application.

FIG. 11 is a schematic structural diagram of an electronic vaporization device in an implementation according to an embodiment of this application. FIG. 12 is a schematic partial exploded structural view of an electronic vaporization device in an implementation according to an embodiment of this application. FIG. 13 is a schematic cross-sectional structural view of an electronic vaporization device in an implementation according to an embodiment of this application. For ease of description, the accompanying drawings only show parts relevant to the embodiments of this application.

Based on the same inventive concept, as shown in FIG. 11 to FIG. 13, an embodiment of this application provides an electronic vaporization device. The electronic vaporization device includes a power supply 70 and the vaporizer described in the foregoing embodiments, and the vaporizer is detachably connected to the power supply 70. Certainly, the electronic vaporization device may also include a shell 60, which is configured to accommodate the vaporizer and the power supply 70 in the shell 60 and is provided for ease of use of the user. In this way, because the vaporization top base 100 described in the foregoing embodiments is used, liquid feeding in the vaporizer is smooth, and the liquid absorption process of the vaporization core 30 is improved to prevent the vaporization core 30 from dry burning, thereby improving the service life of the vaporizer and the use experience of the user.

Based on the above, in the embodiments of this application, by arranging the first corner t1 and the second corner t2 in the liquid feeding channel 120 and utilizing the position relationship between the first corner t1 and the second corner t2, the exit of the liquid feeding channel 120 is enlarged. Meanwhile, the structure of the liquid inlet is improved, so that the liquid inlet is formed by different planes, thereby enlarging an area of the liquid inlet and further improving liquid feeding. On the basis, through the arrangement of the protruding stage 130, the area of the liquid inlet may be enlarged and the space above the vaporization core 30 may be enlarged, liquid feeding may be improved, and weight reduction may be performed on the entire structure. In this way, the liquid feeding space is improved, and the escaping space for bubbles generated when air flows through the liquid feeding channel 120 is enlarged, thereby resolving the problem of obstructed liquid feeding, improving a service life of the vaporizer, and improving the use experience of the user.

The technical features in the foregoing embodiments may be randomly combined. For concise description, not all possible combinations of the technical features in the embodiments are described. However, provided that combinations of the technical features do not conflict with each other, the combinations of the technical features are considered as falling within the scope described in this specification.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article “a” or “the” in introducing an element should not be interpreted as being exclusive of a plurality of elements. Likewise, the recitation of “or” should be interpreted as being inclusive, such that the recitation of “A or B” is not exclusive of “A and B,” unless it is clear from the context or the foregoing description that only one of A and B is intended. Further, the recitation of “at least one of A, B and C” should be interpreted as one or more of a group of elements consisting of A, B and C, and should not be interpreted as requiring at least one of each of the listed elements A, B and C, regardless of whether A, B and C are related as categories or otherwise. Moreover, the recitation of “A, B and/or C” or “at least one of A, B or C” should be interpreted as including any singular entity from the listed elements, e.g., A, any subset from the listed elements, e.g., A and B, or the entire list of elements A, B and C.

What is claimed is:

1. A vaporization top base in communication with a liquid storage cavity of a vaporizer, the vaporization top base comprising:

a top base body comprising a top wall and a side wall surrounding the top wall, the top wall and the side wall encircling to form a vaporization cavity that is independent of the liquid storage cavity and provided with an opening on one end; and at least two liquid feeding channels provided on the top wall, each of the at least two liquid feeding channels being in communication between the liquid storage cavity and the vaporization cavity, wherein a first corner that is arranged close to a central axis of the vaporization cavity and a second corner that is arranged away from the central axis of the vaporization cavity are arranged in each of the liquid feeding channels, and wherein the first corner is arranged upstream of the second corner in a liquid inlet direction.

2. The vaporization top base of claim 1, wherein each of the at least two liquid feeding channels comprises a first liquid inlet provided close to the central axis of the vaporization cavity and a second liquid inlet provided away from the central axis of the vaporization cavity, wherein the first liquid inlet is in communication with the second liquid inlet, and a plane in which the first liquid inlet is located is above a plane in which the second liquid inlet is located in the liquid inlet direction, and wherein the first corner is arranged on a side of the first liquid inlet and the second corner is arranged on a side of the second liquid inlet.

3. The vaporization top base of claim 1, further comprising:

a protruding stage arranged protruding from the top wall, wherein at least a part of the first liquid inlet in each of the at least two liquid feeding channels is provided on the protruding stage, and wherein the second liquid inlet in each of the at least two liquid feeding channels is provided on the top wall.

4. The vaporization top base of claim 3, wherein an air guide channel is provided on the protruding stage, and each of the at least two liquid feeding channels are provided on a periphery of the air guide channel in a circumferential direction, and wherein the first corner in each of the at least two liquid feeding channels is arranged close to an inner side of the air guide channel, and the second corner in each of the at least two liquid feeding channels is arranged away from an outer side of the air guide channel.

5. The vaporization top base of claim 4, wherein the air guide channel comprises an open end and a closed end opposite the open end, wherein the protruding stage comprises vent openings provided on two sides of a central axis of the air guide channel in a first direction, the vent openings being configured to communicate the air guide channel with the vaporization cavity, and wherein the first direction is perpendicular to the central axis of the air guide channel.

6. The vaporization top base of claim 5, wherein a plane in which the closed end of the air guide channel is located and the plane in which the second liquid inlet is located are a same plane or parallel to each other.

7. The vaporization top base of claim 5, wherein a vaporization core of the vaporizer is accommodated in the vaporization cavity, and wherein, in the central axis of the air guide channel, a minimum distance between a surface of a side of the closed end of the air guide channel that faces the vaporization cavity and a top portion of the vaporization core ranges from 1 mm to 3 mm.

8. The vaporization top base of claim 4, wherein the central axis of the air guide channel and the central axis of the vaporization cavity are parallel to each other and/or overlap with each other.

9. The vaporization top base of claim 4, wherein, in the central axis of the air guide channel, a height of the protruding stage ranges from 1.8 mm to 5.5 mm.

10. The vaporization top base of claim 1, wherein, in the liquid inlet direction, a diameter of a cross-section of a part of each of the at least two liquid feeding channels downstream of the first corner ranges from 2 mm to 4 mm.

11. A vaporizer, comprising:

a housing, a liquid storage cavity and an accommodating cavity that are independent of each other being provided in the housing;

a vaporization base arranged in the accommodating cavity, the vaporization base comprising a vaporization bottom base and the vaporization top base of claim 1, and the vaporization bottom base being arranged at the opening to cooperate with the vaporization top base to form the vaporization cavity; and a vaporization core arranged in the vaporization cavity, wherein each of the at least two liquid feeding channels is configured to guide an aerosol-generation substrate in the liquid storage cavity to the vaporization core.

12. The vaporizer of claim 11, wherein an inhalation channel and an air inlet channel are provided in the housing, the inhalation channel being in communication with a top end of the vaporization cavity, the air inlet channel being in communication with a bottom end of the vaporization cavity, and wherein a central axis of the air inlet channel and a central axis of the inhalation channel are parallel to each other and/or overlap with each other.

13. The vaporizer of claim 12, further comprising:

a seal member arranged on a top end of the vaporization top base, wherein a first gap channel is formed between the seal member and the vaporization top base, a second gap channel that is in communication with the air inlet channel is formed between the vaporization base and the accommodating cavity, and the first gap channel is in communication with the air inlet channel through the second gap channel, and wherein a vent hole is provided on the seal member, the vent hole being in communication between the liquid storage cavity and the first gap channel so that the liquid storage cavity is in communication with the air inlet channel.

14. An electronic vaporization device, comprising:

a power supply; and the vaporizer of claim 11, wherein the vaporizer is detachably connected to the power supply.

* * * * *